United States Patent [19]

Mir et al.

[11] Patent Number: 4,857,324

[45] Date of Patent: Aug. 15, 1989

[54] EXOGENOUSLY ACIDIFIED ANTACID COMPOSITIONS HAVING CYTOPROTECTIVE PROPERTIES

[75] Inventors: Ghulam N. Mir, Buckingham, Pa.; Luis E. Borella, Princeton Junction; John F. DiJoseph, Woodbridge, both of N.J.; Gerald L. Reuter, Plattsburgh, N.Y.

[73] Assignee: American Home Products Corporation (Del.), New York, N.Y.

[21] Appl. No.: 135,788

[22] Filed: Dec. 21, 1987

Related U.S. Application Data

[63] Continuation-in-part of Ser. No. 785,417, Oct. 8, 1985, abandoned, which is a continuation-in-part of Ser. No. 831,756, Feb. 20, 1986, abandoned.

[51] Int. Cl.$^4$ .............................................. A61K 33/08
[52] U.S. Cl. ................................... 424/690; 424/682; 424/689; 424/666
[58] Field of Search ........................................ 424/157

[56] References Cited

PUBLICATIONS

J. Wenger et al., J. Clin. Pharmacol., 12:13b, Apr. 1972, pp. 136–141.
L. J. Boyd, et al, Review of Gastroenterology 9:1, pp. 20–25, (Jan.–Feb., 1942).
I. Szelenyi, Acta Physiologica Hungarica, 64(3–4), pp. 259–268, (1984), Functional Cytoprotection by Certain Antacids.
I. Szelenyi et al., European Journal of Pharmacology, 88,403–406, (1983), Evidence for a Functional Cytoprotective Effect Produced by Antacids in the Rat Stomach.

*Primary Examiner*—Frederick E. Waddell
*Attorney, Agent, or Firm*—John W. Routh

[57] ABSTRACT

There are provided gastric cytoprotective exogenously acidified aluminum hydroxide antacid compositions which are formed by acidifying, for example, commercial liquid antacid suspensions containing aluminum hydroxide, antacid powders or solids containing aluminum hydroxide, or aluminum hydroxide gel, to the point where the aluminum hydroxide is solubilized. The solutions may be formulated into liquid dosage forms or spray dried and formulated into solid dosage forms.

16 Claims, No Drawings

EXOGENOUSLY ACIDIFIED ANTACID COMPOSITIONS HAVING CYTOPROTECTIVE PROPERTIES

This application is a continuation-in-part of application Ser. No. 785,417, filed Oct. 8, 1985, now abandoned, and a continuation-in-part of application Ser. No. 831,756, filed Feb. 20, 1986, now abandoned.

The invention relates to exogenously acidified antacid compositions having gastric cytoprotective properties. More particularly this invention relates to exogenously acidified aluminum base containing antacid compositions wherein an antacid suspension has been acidified to the point at which the aluminum ion component is solubilized, and then formulated into liquid dosage forms or for example, spray dried and formulated into solid dosage forms.

BACKGROUND OF THE INVENTION

Gastric cytoprotection not involving the inhibition of gastric acid secretion, is a known phenomenon. For example, prostaglandin F2 does not inhibit gastric acid secretion, but the compound does induce gastric cytoprotection. Other prostaglandins induce gastric cytoprotection at much smaller dose levels than those required for the inhibition of gastric acid secretion. See for example, Shriver, U.S. Pat. No. 4,370,348.

Although the mechanism of cytoprotection by antacids is not clearly defined yet, there is a suggestion that may be partially mediated through the release of gastric mucosal prostaglandins, (Hollander et al, Gastroenterology 86: 1114, 1984 and Tarnawski et al, Gastroenterology 86: 1276, 1984). Szelenyi et al, (Gastroenterology 88: 1604, 1985) has suggested non-prostaglandin mediated mechanisms for cytoprotection.

Activity in the ethanol induced ulcer model is an indication of cytoprotection, regardless of the antisecretory characteristics of the drug. Antisecretory agents, such as the $H_2$ receptor antagonist cimetidine and the anticholinergic agent propantheline bromide do not protect in this model. See Robert et al, Scand. J. Gastroenterol. 19 (Suppl. 101): 69–72, 1984.

The cytoprotective activity of antacids is a recent observation (Hagel et al, Hepato-gastroenterol. 29: 271–274, 1982. Szelenyi et al, Eur. J. Pharmacol. 88: 403–406, 1983. Hollander et al, Gastroenterology 86: 1114, 1984. For example, it has been shown by Szelenyi et al, Gastroenterology 88:5 Part 2, 1604 (1985) and Tarnowski et al, Gastroenterology 86:5, Part 2, 1276 (1985) that $Al(OH)_3$, MAALOX and MYLANTA have cytoprotective properties.

We have demonstrated that magaldrate and other commercially available aluminum base containing antacids inhibit ethanol induced ulcers in rats. The activity of acidified magaldrate in this test suggests, therefore, that it possesses cytoprotective properties as an addition to its acid neutralizing effects.

Antacids have long been thought to exert their antiulcer effects primarily by one of the following mechanisms: (1) acid neutralization, (2) inactivation of pepsin (Piper et al, Am. J. Dig. Dis. 6 (2): 134–141, 1961) and (3) binding to bile salts (Beneyto et al, Arzneim.-Forsch 34 (11): 1350–1354, 1984). The coating of the ulcer crater by antacids has also been considered, but it is not a viable mechanism (Piper, Clinics in Gastro. 2 (2): 361–377, 1973).

In order to substantiate the cytoprotective activity of magaldrate, as distinguished from the other mechanisms of antiulcer activity, 6 N HCl was added to magaldrate to negate its acid neutralization capacity. The pH was changed from approximately 9.0, for a commercial magaldrate suspension to pH 2.5, for acidified magaldrate source. At pH 2.5, acidified magaldrate was significantly more potent in preventing ethanol-induced ulcers in the rat than the commercial magaldrate formula. Therefore, acidified magaldrate fulfills Robert's criteria for a cytoprotective agent, i.e., antiulcer effects at doses which are not antisecretory. Also, the acidified magaldrate was used at low pH (3.0) in a solubilized form in which antacids are reported not able to inactivate pepsin (Wenger et al, J. Clin. Pharmacol. 12: 136–141, 1972. In addition, bile salts are not reported to be involved in ethanol induced ulceration and bile is not visibly present in ethanol treated rat stomachs. Since acid neutralization, pepsin inactivation, and bile binding are not involved in the antiulcer activity of acidified magaldrate in the ethanol model, the contribution of the three viable antiulcer mechanisms to the antiulcer effects of acidified magaldrate has been eliminated and the antiulcer effect of acidified magaldrate can therefore be attributed to its cytoprotective effects.

The above identified article by Wenger et al, J. Clin. Pharmacol. 12:136–141, 1972 entitled "Pepsin Adsorption By Commercial Antacid Mixtures. In Vitro Studies" describes the adsorption of pepsin by various commercial antacid mixtures independently of their effect on pH. In the experiments, antacid dilutions were prepared by adding 10 grams of certain commercial antacid suspensions to 100 milliliters of distilled water. Using hydrochloric acid and distilled water, the concentration was further decreased to 5 grams per 100 milliliters. For each mixture four flasks were prepared and the final pH of each was brought to 1.5, 3.0, 5.0 and 6.0. The antacids included Gelusil-M, Delcid, Maalox, Riopan and Amphojel. The article refers to other authors who have similar acidified antacid solutions.

Experimental duplication of the Wenger et al Riopan antacid dilution prior to acidification has established that the Wenger et al Riopan antacid dilution does not meet the Food and Drug Administration requirements since its neutralizing capacity is less than half of the FDA requirement. Hence, the Riopan antacid dilution of Wenger et al prior to acidification is not a precursor pharmaceutically acceptable antacid composition required by this invention.

SUMMARY OF THE INVENTION

In accordance with this invention, there is provided gastric cytoprotective exogenously acidified aluminum base containing compositions which are formed by acidifying, for example, commercial liquid antacid suspensions containing an aluminum base such as aluminum hydroxide, antacid powders or solids containing an aluminum base such as aluminum hydroxide, or aluminum hydroxide gel, to the point where the aluminum base is solubilized. The end point for the solubilization is ordinarily in the range of about pH 2.25 to 3.25 and the acidified composition has a concentration of about 50 to about 98 grams of precursor aluminum base containing composition prior to acidification per 100 milliliters of acidified composition.

The gastric cytoprotective compositions are pharmaceutically cytoprotective exogenously acidified aluminum base containing compositions acidified to a pH between about 2.25 to about 3.25 at which the aluminum base component is solubilized and obtained by exogenous acidification of a precursor aluminum base containing pharmaceutically acceptable antacid composition and having a concentration of about 50 to about 98 grams of precursor antacid composition prior to acidification per 100 milliliters of acidified composition.

By the term antacid composition as used in this specification and claims is meant a pharmaceutically acceptable antacid composition meeting the requirements of the U.S. Food and Drug Administration in terms of minimal buffering capacity, i.e. that the antacid composition must neutralize at least 5 milliequivalents of acid and must maintain a pH of 3.5 for 10 minutes in a defined in vitro test described in 21 CFR 33.26. See "Handbook of NonPrescription Drugs," Eighth Edition, page 32, published by the American Pharmaceutical Association.

In another embodiment of this invention, the exogenously acidified compositions containing solubilized aluminum base are further formulated into liquid dosage forms such as syrups, or, for example, the solutions are spray dried and formulated into solid dosage forms such as powders for encapsulation or compression into tablets.

DETAILED DESCRIPTION OF THE INVENTION

Aluminum hydroxide is aluminum hydrate, aluminum trihydrate of hydrated alumina of formula $Al(OH)_3$. The aluminum hydroxide is described only as a gastric antacid (see the Merck Index, 8th Edition p 44).

Acidified aluminum hydroxide, according to the present invention, is produced by treating an aqueous gel or suspension of aluminum hydroxide with an acid such as aqueous hydrochloric acid until the suspension becomes solubilized.

Magaldrate is a magnesium aluminate hydrate, described in Hallmann et al, U.S. Pat. No. 2,923,600. Extra strength magaldrate and rehydratable magaldrate are disclosed and claimed respectively in Wu et al. U.S. Ser. No. 661,648, filed Oct. 17, 1984, and Wu et al U.S. Ser. No. 765,898, filed Aug. 14, 1985, both of which applications are herein incorporated by reference in their entirety.

Magaldrate is a chemical union of aluminum and magnesium hydroxide, corresponding approximately to the formula $Al_5Mg_{10}(OH)_{31}(SO_4)_2xH_2O$, according to the official monograph USP XX, third supplement USP-NF, and has a molecular weight of about 1097. Magaldrate, also sometimes referred to in said monograph as aluminum magnesium hydroxide sulfate, contains not less than 29.0 percent and not more than 40.0 percent of magnesium oxide ($M_gO$) and the equivalent of not less than 18.0 percent and not more than 26.0 percent of aluminum oxide ($Al_2O_3$).

The preparation of magaldrate is described in U.S. Pat. No. 2,923,660. A commercially suitable precedure is described in said patent, for example, beginning in column 2, line 40. Aluminum sulfate is employed as at column 2, line 58 in order to obtain a magaldrate "all sulfate" material and, to maintain a low sodium content for the final product, the use of potassium oxide (or hydroxide) is preferred over the disclosed sodium oxide. Typically the magaldrate is precipitated to provide a 6% weight/volume mixture (fluid when fresh) and diluted to 3% for washing prior to concentration and formulation into a suspension providing a so called single strength acid neutralization capacity (ANC) of 13.5 to 15 meq per 5 milliliters of suspension which is equivalent to a magaldrate weight/weight concentration in the range of about 12 to 13 percent solids. At this concentration, unformulated magaldrate is a paste-like gel. Formulated magaldrate is sold under the RIOPAN trademark.

In addition to aluminum hydroxide gel and magaldrate gel described above, suitable starting materials also include other aluminum hydroxide-magnesium hydroxide gels prior to formulation into commercial antacid compositions and spray dried powders formed from such gels.

Surprisingly, antacid compositions based on aluminum phosphate, when acidified, do not exhibit cytoprotective activity. Also, aluminum chloride does not exhibit such activity.

Suitable commercial liquid antacids for preparing the acidified compositions of this invention include for example, AMPHOJEL and ALUDROX marketed by Wyeth Laboratories, Inc. of Philadelphia, Pa., RIOPAN, RIOPAN PLUS and RIOPAN Extra Stength marketed by Ayerst Laboratories, Inc. New York, N.Y., MAALOX, MAALOX PLUS and MAALOX TC marketed by William H. Rorer, Inc. Fort Washington, Pa., MYLANTA and MYLANTA II marketed by Stuart Pharmaceuticals, Wilmington, Delaware, and DI-GEL marketed by Plough, Inc., Memphis Tenn.

MAALOX Suspension (manufactured by Rorer, Physicians' Desk Reference for Nonprescription Drugs 6th ed. 1985) is a combination of magnesium and aluminum hydroxides containing 225 mg aluminum hydroxide equivalent to dried gel USP, and 200 mg magnesium hydroxide per 5 ml of suspension. Each 5 ml of MAALOX Suspension neutralizes 13.3 mEq of acid. MYLANTA (manufactured by Stuart, Physicians' Desk Reference for Nonprescription Drugs 6th ed. 1985) is a liquid containing 200 mg aluminum hydroxide, 200 mg magnesium hydroxide and 20 mg simethicone per 5 ml of liquid. Each 5 ml of MYLANTA liquid neutralizes 12.7 mEq. of acid.

The acidification of the antacids should be accomplished with care so that the end point does not drop much below the pH at which the suspension becomes a solution or at which the aluminum hydroxide is solubilized. This is to minimize formation of other aluminum species. Thus the gel preferably is diluted with water or the solid rehydrated with water prior to acidification.

Suitable acids for acidification include the mineral acids hydrochloric, nitric and sulfuric acids, phosphoric acid and the organic acids such as acetic acid, lactic acid, citric acid and propionic, glycolic, lactic, adipic and maleic acids. If the organic acids do not give a clear to translucent solution at a pH of about 2.25 to about 3.25, then the addition of a small amount of hydrochloric acid usually will provide a near clear or translucent solution. Sulfuric acid in high concentration causes an exothermic reaction sufficient to char the antacid suspensions so must be used with care.

This invention is directed to the use of acidified antacids as cytoprotective agents. Cytoprotection mechanisms are not well defined. However, it is clear that lower dosages of cytoprotective agents are required for effectiveness than are required to inhibit gastric acid secretions. Because of its cytoprotective nature, exogenously acidified antacids may be used to treat or prevent disease states such as gastric and duodenal ulcers, regional ileitis, Crohn's disease, erosive gastritis, erosive esophagitis, inflammatory bowel disease and ethanol-induced hemorrhagic erosions.

The acidified antacid compositions may be administered along or concomitantly or in combination with another active drug including an $H_2$ blocker such as cimetidine and ranitidine, an antispasmotic such as a belladonna alkaloid, or another medicinal product which may be irritating to the gastrointestinal tract such as aspirin, ibuprofen, acetaminophin, and azulene.

Any suitable dosage form may be employed for providing a mammal, especially a human with the effective dosage of acidified antacid. For example, suitable dosage forms include tablets, troches, dispersions, suspensions, solutions, suppositories, capsules and the like for oral, parenteral or rectal administration.

A convenient dosage form is to directly administer the acidified antacid solution. However, in practice the acidified antacid solution may be spray dried. The dry powder can be combined as the active ingredient in intimate admixture with a pharmaceutical carrier according to conventional pharmaceutical compounding techniques. The carrier may take a wide variety of forms depending on the form of preparation desired for administration.

In preparing the compositions for oral dosage form, any of the usual pharmaceutical media may be employed, such as, for example, water, glycols, oils, flavoring agents, preservatives, coloring agents and the like in the case of oral liquid preparations, such as, for example, suspensions, emulsions and solutions; or carriers such as starches, sugars, diluents, granulating agents, lubricants, binders, disintegrating agents and the like in the case of oral solid preparations such as, for example, powders, capsules and tablets. Because of their ease of administration, tablets and hard or soft gelatin capsules represent the most advantageous oral dosage unit form, in which case solid pharmaceutical carriers are obviously employed. If desired, tablets may be sugar coated or otherwise coated by standard techniques.

In addition to acidified antacid the pharmaceutical composition may also contain other active ingredients, such as non-steroidal anti-inflammatory agents e.g., etodolac, indomethacin, ibuprofen, sulindac, fenbufen, and the like, or peripheral analgesic agents such as zomepirac, diflunisal and the like.

EXAMPLE 1

A magaldrate suspension product according to Example 4 of Wu et al U.S. Pat. No. 4,704,278, having an ANC of 30 meq/5 ml of magaldrate, 1080 mg/5 ml of suspension was prepared as follows. The formula given is for 1 liter (1.18 Kg). This is the approximate formula for commercial RIOPAN Extra Strength suspension.

| Ingredient | Amount |
| --- | --- |
| Magaldrate Gel (sulfate, potassium base) | 2.93 l* |
| Aluminum Hydroxide Gel (12.5% $Al_2O_3$) | 47.8 g |
| Potassium Citrate | 19.6 g |
| Sorbitol Solution (70%) | 57.4 g |
| Glycerin | 47.8 g |
| Saccharin | 0.383 g |
| Xanthan Gum | 1.43 g |
| Peppermint, Natural and Artificial | 0.283 ml |
| Monochloramine Solution (sanitizer) | q.s. sufficient quantity to give 100 p.p.m. |
| Water, purified, Chlorinated q.s. | 1.18 Kg. |

*Theoretical input per liter is a 216 g Magaldrate at 100%

1. In a suitable tank equipped with a mixer, the sorbitol solution, 15.7 g of the water and the citrate were combined and then mixed until a clear solution was obtained. The aluminum hydroxide gel was added and mixed until uniform and mixing continued until use.

2. Immediately before concentration of the magaldrate gel, 126 g of the Step #1 mixture was added to a jacketed tank equipped with a stirrer. With continuous stirring, the magaldrate gel was concentrated on a rotary filter to a concentration of not less than 24% w/w into the mixture and cooling to 25° C. was begun. After all the concentrated antacid had been added the remainder of the Step #1 mixture was added with continuous stirring to achieve uniformity.

3. The Step #2 mixture was processed through a homogenizer into a jacketed tank with continuous stirring and continuous cooling to 25° C.

4. The remaining ingredients, except the water and monochloramine, were mixed in a separate container until uniform, after which, they were added to the magaldrate mixture and mixed until the xanthan gum was hydrated. Water was then added (with mixing) to bring the batch up to about 1.18 Kg.

The acidified extra strength magaldrate of this invention was prepared by adding 6 N HCl to an endpoint of pH 2.5 as determined by a Corning, Model 7, pH meter. Equilibration was achieved over 12 hours. At this endpoint, the antacid suspension became solubilized. This indicates a dissolution of the active antacid species. The dose volume of antacid was adjusted for the volume of 6N HCl added to the suspension.

EXAMPLE 2

Acidified MAALOX of the present invention was prepared by adding to a sample of commercial MAALOX 6 N HCl to an endpoint of pH 3.0 as determined by a Corning, Model 7, pH meter. Equilibration was achieved over 12 hours. At this endpoint, the antacid suspension became solubilized indicating a dissolution of the active antacid species.

EXAMPLE 3

Acidified MYLANTA, of the present invention, was produced by treating a sample of commercial MYLANTA liquid with 6N hydrochloric acid until a pH of 3.0. At this pH the antacid suspension became solubilized, again indicating a dissolution of the active antacid species.

EXAMPLE 4

Aluminum hydroxide gel of commercial grade was admixed with and suspended in water to yield a suspension containing the equivalent of 133 mg $Al_2O_3$ per ml. The suspension was then acidified with 6N HCl until the aluminum hydroxide was solubilized at an end point of pH 3.0. A clear solution resulted.

EXAMPLE 5

A sample of commercial BASALJEL marketed by Wyeth Laboratories, Inc., Philadelphia, Pa., was acidified by adding 6N HCl to an endpoint of pH 2.5 as determined by a Corning Model 7 pH meter. BASALJEL contains dried basic aluminum carbonate and the acidification was accompanied by copious gas evolution. The suspension prior to acidification contained the equivalent of 200 mg aluminum hydroxide per ml.

EXAMPLE 6

A sample of commercial PHOSPHALJEL marketed by Wyeth Laboratories, Inc., of Philadelphia, Pa. was acidified by adding 6 N HCl to an endpoint of pH 2.5. PHOSPHALJEL contains 46.6 mg aluminum phosphate per ml.

EXAMPLE 7

The cytoprotective activity of a compound may be observed in both animals and man by noting the increase resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

The ethanol-induced lesion assay is a standard test for cytoprotective activity and is described in an article by A. Robert et al entitled "Cytoprotection By Prostaglandins in Rats" published in Gastroenterology 77:433–443, 1979.

The ethanol-induced lesion assay was used to measure the cytoprotective ability of commercial antacids. Male Sprague-Dawley rats (supplier, Charles River, Willmington, Mass.) weighing between 120–150 g were used. The rats were fasted for 24 hr prior to use (water ad libitum). Before dosing, the animals were placed two per cage and denied water.

Animals were orally, i.e. intragastrically pretreated, one hour before ethanol administration with either RIOPAN Extra Strength suspension, MAALOX suspension, $PGE_2$, or vehicle. One hour after ethanol administration, the rats were sacrificed by $CO_2$ asphyxiation. The stomachs were removed and kept moist with saline until the lesions were scored. Ulcers were scored with the investigator unaware of the treatment groups (single blind). Ulcers were graded according to the following scale:

| GRADE | DESCRIPTION (Approximate length of lesion) |
|---|---|
| 0 | no lesion |
| 1 | 2 mm or less |
| 2 | 4 mm |
| 3 | 6 mm |

Absolute ethanol was given orally, 1 ml/rat. RIOPAN Extra Strength, 1080 mg magaldrate per 5 ml (lot 3RM4), and MAALOX, 200 mg $Mg(OH)_2$ + 225 mg $Al(OH)_3$ per 5 ml (lot 64700), were administered orally as commercially available suspensions. The dose volume administered was based on the $ED_{50}$ (ml of antacid/kg, see Table 1).

The dose volume of acidified antacid was adjusted for the volume of 6 N HCl added to the suspension. $PGE_2$ was stored in 100% ethanol and diluted with normal saline before use.

Magaldrate of Example 1 and MAALOX of Example 2 were prepared as described above. The dose volume of nonbuffering antacid was adjusted for the volume of 6 N HCl added to the suspension during preparation. $PGE_2$ was stored in 100% ethanol and diluted with normal saline before use.

RESULTS

The mean ulcer score of each treatment group was compared to the control group and expressed as the percent inhibition of ulcer formation.

The cytoprotective $ED_{50}$ before and after acidification for the magaldrate of Example 1, referred to in this example as RIOPAN Extra Strength, and for MAALOX of Example 2 was calculated by standard regression analysis of the dose-response data. Confidence limits of 95% were calculated using the statistical differential method.

RIOPAN Extra Strength and the MAALOX of Example 2 respectively prior to acidification each produced a dose dependent reduction in ulcer score (FIG. 1). When calculated on the basis of weight of antacid administered, the $ED_{50}$ for magaldrate and MAALOX were not significantly different (453.6 mg/kg for magaldrate and 374 mg/kg for MAALOX, (Table 1).

At pH 2.5, RIOPAN Extra Strength was solubilized in accordance with this invention. It produced a dose dependent reduction in ulcer score ($ED_{50}$ = 58.3 mg/kg). Acidified magaldrate was significantly more potent than commercial magaldrate in inhibiting ulcer formation (Table 1).

MAALOX was solubilized at pH 3.0 in accordance with this invention. The solubilized acidified MAALOX reduced the ulcer score dose dependently and was significantly more potent than commercial MAALOX (Table 1). There was no statistical difference in the antiulcer $ED_{50}$'s calculated for acidified magaldrate and acidified MAALOX (Table 1).

Effect of regular and acidified RIOPAN Extra Strength suspension and MAALOX suspension on ethanol induced gastric ulcers in the rat as discussed above is shown in Table 1 below:

TABLE I

| Antacid | Dose:Per Os ml Antacid Suspension per Kg | MG ANT-ACID per Kg | % Inhibition | $ED_{50}$ = mg/kg (95% C)* |
|---|---|---|---|---|
| RIOPAN Extra Strength (commercial) | 8 | 1728 | 76 | 453.6 |
|  | 2 | 432 | 42 | (237.6–799.2) |
|  | 0.5 | 108 | 30 |  |
| RIOPAN Extra Strength (acidified) | 1 | 216 | 86 | 58.3 |
|  | 0.5 | 108 | 77 | (38.9–86.4) |
|  | 0.25 | 54 | 44 |  |
| MAALOX (commercial) | 20 | 1700 | 85 | 374 |
|  | 5 | 425 | 51 | (212.5–646.0) |
|  | 1 | 85 | 18 |  |
| MAALOX (acidified) | 1 | 85 | 76 | 43.4 |
|  | 0.3 | 25.5 | 24 | (28.1–63.8) |
|  | 0.1 | 8.5 | 3 |  |

*Cytoprotective $ED_{50}$

It was found that RIOPAN Extra Strength and MAALOX dose dependently reduced ethanol-induced gastric ulcers in the rat ($ED_{50}$ = 453.6 mg/kg, p.o., and $ED_{50}$ = 374.0 mg/kg, p.o., respectively). The recommended human dose of RIOPAN Extra Strength (10 ml) corresponds to an oral dose of 43 mg/kg of magaldrate, and for MAALOX (20 ml), an oral dose of 34 mg/kg of antacid for a 50 kg person. RIOPAN Extra Strength and MAALOX were acidified in accordance with this invention by the addition of 6 N HCl to an endpoint of pH 2.5 for RIOPAN Extra Strength and pH 3.0 for MAALOX. Acidified RIOPAN Extra Strength and MAALOX dose dependently reduced ethanol-induced gastric ulcers ($ED_{50}=58.3$ mg/kg, p.o., and $ED_{50}=43.4$ mg/kg, p.o., respectively). Acidified RIOPAN Extra Strength and acidified MAALOX were about eight fold more potent than commercial RIOPAN Extra Stength and MAALOX in inhibiting ethanol-induced ulcers in rat. RIOPAN Extra Strength and MAALOX were cytoprotective in the ethanol-induced gastric cytotoxicity model in the rat. Hence the recommended human dose of the acidified antacid composition of the invention is about one-eighth of the recommended dose of the precursor antacid composition prior to acidification.

When tested at their $ED_{50}$ doses, both RIOPAN Extra Strength and MAALOX, commercial and acidified, significantly inhibited ethanol induced gastric ulcers when compared with vehicle (physiological saline) treated rats (Table 2).

TABLE 2

Effect of the oral $ED_{50}$ dose of commercial and acidified RIOPAN Extra Strength and MAALOX on ethanol induced gastric ulcers in rat.

| ANTACID | DOSE, MG/KG P.O. | % INHIBITION |
| --- | --- | --- |
| RIOPAN Extra Strength (commercial) | 453.6 | 61* |
| RIOPAN Extra Strength (acidified) | 58.3 | 50* |
| MAALOX (commercial) | 374.0 | 60* |
| MAALOX (acidified) | 43.4 | 56* |

*p .01, significantly different from vehicle treated group, Dunnett's multiple comparison test.

Examples 4 through 6 are summarized with respect to antacid content in Table 3.

TABLE 3

| Antacid | Dose:Per Os ml Antacid Suspension per Kg | % Inhibition | $ED_{50}$ = mg/kg (95% C)* |
| --- | --- | --- | --- |
| Aluminum Hydroxide Gel (Example 4) | 0.1<br>0.5<br>2.0 | 6<br>65<br>74 | 66.5 |
| BASALJEL Extra Strength (Example 5) | 0.1<br>0.5<br>2.0 | 30<br>65<br>73 | 120 |
| PHOSPHALJEL (Example 6) | 0.5<br>2.0<br>8.0 | 12<br>25<br>65 | 14 |

*Cytoprotective $ED_{50}$

It can be seen from these data that the acidified aluminum phosphate containing antacid is relatively weak in cytoprotective activity as compared with the products of Examples 4 and 5. This is probably because it contains less basic aluminum than the others.

$PGE_2$ inhibited ethanol induced ulcer formation (Table 3). $PGE_2$ was approximately 1000 times more potent than either acidified RIOPAN Extra Strength or acidified MAALOX.

TABLE 4

Effect of $PGE_2$ on ethanol induced gastric ulcers in rat.

| DOSE, g/kg P.O. | % INHIBITION | $ED_{50}$ g/kg (95% CI) |
| --- | --- | --- |
| $PGE_2$ 75 | 80 | 34.1 |
| 50 | 63 | (27.3–42.3) |

TABLE 4-continued

Effect of $PGE_2$ on ethanol induced gastric ulcers in rat.

| DOSE, g/kg P.O. | % INHIBITION | $ED_{50}$ g/kg (95% CI) |
| --- | --- | --- |
| 25 | 39 | |

As indicated above, inducement of gastric cytoprotection by acidified antacids is unrelated to the inhibition of gastric acid secretion. Although the mechanisms of gastric cytoprotection is unknown, it appears the cytoprotective acidified antacids increase the resistance of gastric mucosal cells to the necrotizing effect of strong irritants. It is suggested, therefore, that nonbuffering antacids by a mechanism other than inhibition of gastric acid secretion, maintain the integrity of the gastric mucosa and will thus be beneficial in the treatment of those disease states wherein injury to the gastric mucosa is present.

Based on the data obtained in these assays, the effective oral dosage level to obtain cytoprotective effects from the exogenously acidified aluminum hydroxide containing compositions of this invention derived from commercial antacids is about one-eighth the oral dosage level of the active antacid component or ingredients of the respective commercial antacid. Such oral dosage levels of commercial antacids appear on their labels and generally range from 200 to 400 milligrams of aluminum hydroxide per dose or 400 to 600 milligrams of magaldrate per dose. Accordingly, the dosage levels of the liquid and solid cytoprotective compositions of this invention can range from about one-eighth to the equivalent dose of the precursor antacid or aluminum base.

EXAMPLE 8

In the following examples, acidified antacids similar to those of Examples 1 through 4 were spray dried. In these examples a Buchi 190 Mini Spray Drying was employed to dry the acidified antacids. This model spray dryer is manufactured by Buchi Laboratoriums-Technik AG. Other spray dryers can be employed, however, such as those manufactured by Anhydro Company of Attleboro, Mass. and Niro Atomizer Inc., of Columbia, Md., so long as the spray dryer can process the relatively viscous admixture. The operating conditions for the Buchi 190 Mini Spray Dryer are customarily an inlet temperature of 220° C., and an outlet temperature of 130° C. Since the acidified antacids are corrosive, special nozzles should be employed such as those fabricated from titanium.

In this example, 12 fluid ounces of commercial MAALOX TC suspension were acidified with 10N HCl q.s. ad pH 2.5 to form a yellow color solution. The solution contained approximately 72 grams of antacid suspension per 100 ml of solution and approximately 43 grams of aluminum hydroxide per 600 ml of solution. The solution was spray dried to yield a non-flowing white powder.

EXAMPLE 9

In this example, 12 fluid ounces of commercial RIOPAN Extra Strength suspension were admixed with 32 grams of amorphous silicon dioxide and then acidified with 10N HCl q.s. ad pH 2.5 to yield an off white dispersion. The white dispersion contained approximately 78 grams of antacid suspension per 100 ml. of white dispersion and approximately 13 grams of magaldrate per 100 ml of white dispersion. The dispersion was spray dried to yield a sticky white semisolid.

EXAMPLE 10

A placebo without magaldrate and aluminum hydroxide was prepared having the approximate formula of Example 1. In this example, 500 ml of the placebo admixture was acidified with 10N HCl q.s. ad pH 2.5. The admixture was processed through the spray drier but a powder was not obtained.

EXAMPLE 11

In this example, 600 grams of magaldrate gel which had been spray dried for commercial tablet production, were acidified with 10N HCl q.s. ad pH 2.5 to yield a yellow color solution which spray dried to a fluffy white powder. The yellow solution contained approximately 83 grams of magaldrate per 108 ml of yellow solution.

EXAMPLE 12

In this example, 12 fluid ounces of commercial MYLANTA suspension were acidified with 10N HCl q.s. ad pH 2.5 to yield a translucent dispersion. The translucent dispersion contained approximately 83 grams of antacid suspension per 100 ml of translucent dispersion and approximately 3 grams of aluminum hydroxide per 100 ml. translucent dispersion. The dispersion was spray dried to give an off-white to gray powder.

EXAMPLE 13

In this example, 12 fluid ounces of commercial MAALOX suspension were acidified with 10N HCl q.s. ad pH 2.5 to yield a near-clear dispersion. The near clear dispersion contained approximately 69 grams of antacid suspension per 100 milliliters of clear dispersion and approximately 3 grams of aluminum hydroxide per 100 milliliters of near clear dispersion. The dispersion was spray dried to give a fluffy white powder.

EXAMPLE 14

In this example, 12 fluid ounces of commercial AMPHOJEL suspension were acidified with 10N HCl q.s. ad pH 2.5 to yield a translucent dispersion. The translucent dispersion contained approximately 88 grams of antacid suspension per 100 milliliters of translucent dispersion and approximately 5 grams of aluminum hydroxide per 100 milliliters of translucent dispersion. The dispersion was spray dried to give a white powder.

EXAMPLE 15

In this example, 100 grams of a rehydratable magaldrate powder were used. The rehydratable magaldrate powder was prepared in accordance with Example 1 of Wu et al patent U.S. Pat. No. 4,676,984 issued June 30, 1987 as follows:

| INGREDIENTS | AMOUNT |
| --- | --- |
| Magaldrate Gel Sulfate, Potassium Based (7.38%) | 90.0 kg |
| Potassium Citrate, NF | 1.47 kg |
| Aluminum Hydroxide Gel, Guilini, A671/4 | 1.85 kg |
| Sorbitol Solution, USP | 2.85 kg |

The above listed ingredients were processed as set forth below. Continuous agitation must be maintained throughout the processing.

Step 1. Add the sorbitol solution, USP to a suitable tank equipped with a stirrer.

Step 2. Add the potassium citrate, NF then mix until uniform.

Step 3. Concentrate the magaldrate gel sulfate, potassium base to not less than 24% magaldrate and add to the tank in Step #2

Step 4. When approximately half of the concentrated gel has been added to the batch, add the aluminum hydroxide gel to the mixture of Step #3.

Step 5. When all of the gel has been added, obtain an assay of the magaldrate content and adjust the quantities of all ingredients to the theoretical ratios. Mix for 5 minutes after each addition.

Step 6. Spray dry the Step #5 gel mixture at the following conditions:
Inlet: 400° C.
Outlet: 130° C.
Wheel Speed: 20,000 RPM A sample of 100 grams of this rehydratable magaldrate powder was acidified with 10N HCl q.s. ad pH 2.5 to yield an opaque liquid. The opaque liquid contained approximately 95 grams of rehydratable magaldrate powder per 100 milliliters of opaque liquid and 62 grams of magaldrate per 100 milliliters of opaque liquid. The liquid was spray dried to give a white powder.

Examples 8 through 15 are summarized with respect to antacid content in Table 5.

TABLE 5

|  | Grams Antacid Suspension per 100 ml Acidified Composition | Grams $Al(OH)_3$ per 100 ml Acidified Composition | Grams Magaldrate per 100 ml Acidified Composition |
| --- | --- | --- | --- |
| MAALOX TC | 72 | 7 |  |
| RIOPAN Extra Strength | 78 |  | 13 |
| Spray Dried Magaldrate Gel | 83 |  | 83 |
| MYLANTA | 83 | 3 |  |
| MAALOX | 69 | 3 |  |
| AMPHOJEL | 88 | 5 |  |
| Rehydratable Magaldrate Powder | 95 |  | 62 |

Instead of spray drying the acidified liquids as described in Examples 8 through 15, the liquids can be admixed with liquid or dry excipients and subjected to tray, drum, spin or flash drying.

EXAMPLE 16

The spray dried powders of Examples 8 through 15 were tested for cytoprotective activity in the ethanol-induced lesion assay as described in Example 7.

The respective powders were admixed with sufficient water to form a liquid and the animals were dosed 400 milligrams of powder per kilo of body weight per oz. in the test. The results are shown in Table 6 below:

TABLE 6

| Example | Antacid | % Inhibition |
| --- | --- | --- |
| 8 | MAALOX TC | 87% |

TABLE 6-continued

| Example | Antacid | % Inhibition |
|---|---|---|
| 9 | RIOPAN Extra Strength | 89% |
| 10 | Placebo | 0% |
| 11 | Spray Dried Magaldrate Gel | 97% |
| 12 | MYLANTA | 82% |
| 13 | MAALOX | 98% |
| 14 | AMPHOJEL | 98% |
| 15 | Rehydratable Magaldrate | 80% |

EXAMPLE 17

In this example, a 100 gram sample of magaldrate gel which had been spray dried to manufacture commercial magaldrate tablets was acidified q.s. ad pH 2.5 with the various acids as shown in Table 7.

TABLE 7

| | |
|---|---|
| Hydrochloric acid: | Yields a yellow solution |
| Phosphoric acid: | Yields a clear water white solution |
| Sulfuric acid: | Yields a clear water white solution with an exothermic reaction. High concentrations of acid produce a charred mass. |
| Nitric acid: | Yields a near clear white dispersion. |
| Acetic acid: | Yields a translucent to opaque dispersion. This dispersion when further treated with hydrocloric acids yields a near clear light yellow color dispersion. |
| Lactic acid: | Yields an opaque suspension. |
| Citric acid: | Yields a translucent to opaque suspension. |

EXAMPLE 18

In this example, a combination dosage form is prepared containing aspirin and the spray dried acidified magaldrate gel of Example 11 with the ingredients listed below loaded into a hard gelatin capsule in the indicated amounts.

| Ingredients | Amount |
|---|---|
| Aspirin, USP | 600 mg |
| Product of Example II | 100 mg |
| Lactose, USP | 200 mg |

The above ingredients are mixed in a V-Blender and then compressed to fill a No. 0 hard gelatin capsule.

EXAMPLE 19

In this example, a combination dosage form is prepared containing acetaminaphin and the spray dried acidified magaldrate gel of Example 11 with the ingredients listed below compressed into a tablet.

| Ingredients | Amount |
|---|---|
| Acetaminophin, USP | 325 mg |
| Product of Example II | 100 mg |
| Microcrystalline cellulose, NF | 200 mg |
| Stearic acid, NF | 10 mg |

The above ingredients are mixed in a V-Blender and then compressed in a tablet press to form a tablet.

EXAMPLE 20

In this example, a combination dosage form is prepared containing ibuprofen and the spray dried acidified magaldrate gel of Example 11 with the ingredients listed below loaded into a hard gelating capsule in the indicated amounts.

| Ingredients | Amount |
|---|---|
| Ibuprofen | 200 mg |
| Product of Example II | 100 mg |
| Starch | 200 mg |

The above ingredients are mixed in a V-Blender and then compressed to fill a No. 4 hard gelatin capsules.

EXAMPLE 21

In this example, the acidified antacid compositions of this invention, prepared according to Example 7, were compared for cytoprotective activity with both a commercial RIOPAN Extra Strength suspension and acidified RIOPAN solutions having a pH of 1.5 and a pH of 3 made in accordance with the teaching of the Wenger et al publication referred to above in the Background Of The Invention.

The experiments were performed using ten rats for each test composition and using the in vivo test procedure described in Example 7. The dose of acidified Extra Strength RIOPAN was selected for the test at 0.46 milliliters per kilogram of rat body weight. Approximately 4.6 times this amount (8 times on a mg/kg basis) was selected for the dose of commercial Extra Strength RIOPAN. Approximately 30 times this amount was selected for each dose of the Wenger et al solutions. The results are shown in Table 7 below:

TABLE 7

| Antacid | Dose:Per Os ml Antacid Suspension per Kg | MG ANTACID per Kg | % Inhibition |
|---|---|---|---|
| RIOPAN Extra Strength (commercial) | 2.1 | 453 | 58% |
| RIOPAN Extra Strength (acidified) | 0.46 | 58.3 | 94% |
| Wenger et al pH 1.5 | 15.3 | 58.3 | 89% |
| Wenger et al pH 3.0 | 15.3 | 58.3 | 72% |

The results of the experiments are shown in Table 7 and can be summarized as follows:

(a) the test scores establish that the acidified Extra Strength RIOPAN of the invention gave an equivalent percent inhibition as the Wenger et al solutions given at a more than 30 times larger dose.

(b) from the viewpoint of a pharmacist, a pharmaceutical dosage form should be as easy and pleasant to administer as possible in order to assure patient compliance, and that a third of a teaspoon of a liquid medicine is easier and more pleasant to administer than three teaspoons of a liquid medicine.

EXAMPLE 22

In this example the same test solutions were used as in Example 21 and experiments were performed to establish the percent inhibition of the Wenger et al solutions at the same dose level as compared commercial magaldrate and to the acidified magaldrate of this invention.

Two experiments were performed using ten rats for each test composition and again using the in vivo test procedure described in Example 7. In these experiments the dose in milliliters per kilogram of rat body weight was equal for each test composition. The results are shown in Table 8 below:

TABLE 8

| Antacid | Dose:Per Os ml Antacid Suspension per Kg | MG ANTACID per Kg | Experiment 1 % Inhibition | Experiment 2 % Inhibition |
|---|---|---|---|---|
| RIOPAN Extra Strength (commercial) | 1 | 216 | 55 | 47% |
| RIOPAN Extra Strength (acidified) | 1 | 127 | 93 | 99% |
| Wenger et al pH 1.5 | 1 | 3.8 | 9% | 23% |
| Wenger et al pH 3.0 | 1 | 3.8 | 35% | 23% |

The results of the experiments shown in Table 8 and can be summarized as follows:

(a) In the first experiment, the dose of acidified Extra Strength RIOPAN gave a 93% inhibition against ulcer formation whereas the commercial Extra Strength RIOPAN gave a 55% inhibition and the Wenger et al solutions gave inhibitions of 9% to 35%.

(b) In the second experiment, the dose of acidified Extra Strength RIOPAN gave a 99% inhibition against ulcer formation whereas the commercial Extra Strength RIOPAN gave a 47% inhibition and the Wenger et al solutions gave inhibitions of 23%.

(c) The tests do not show any significant biological activity for the Wenger et al solutions at this dose.

Useful dosage forms for the acidified magaldrate powder are described in co-pending patent application Ser. No. 121,971, filed Nov. 18, 1987 and comprise pharmaceutical dosage forms for oral administration comprising a gelatin capsule encapsulating an admixture of the acidified magaldrate spray dried powder with an at least partially hydrogonated and/or solidified vegetable oil.

What is claimed is:

1. A pharmaceutically cytoprotective exogenously acidified aluminum base containing composition acidified to a pH between about 2.25 to about 3.25 at which the aluminum base component is solubilized and obtained by exogenous acidification of a precursor aluminum base containing antacid composition and having a concentration of about 50 to about 98 grams of precursor antacid composition prior to acidification per 100 milliliters of acidified composition, the precursor antacid composition having an acid neutralizing capacity of at least 5mEq.

2. The cytoprotective composition of claim 1 wherein the aluminum base is aluminum hydroxide.

3. The cytoprotective composition of claim 2 also containing solubilized magnesium hydroxide.

4. The cytoprotective composition of claim 1 wherein the composition has been acidified with hydrochloric acid.

5. The cytoprotective composition of claim 1 wherein the antacid composition is commercial antacid composition.

6. The cytoprotective composition of claim 5 wherein the antacid composition is magaldrate.

7. The cytoprotective composition of claim 1 wherein the antacid composition is aluminum hydroxide gel.

8. The cytoprotective composition of claim 1 wherein the antacid composition is magaldrate gel.

9. A cytoprotective spray dried solid formed from an exogenously acidified liquid aluminum hydroxide containing composition acidified to a pH at which the aluminum hydroxide content is solubilized and then spray dried.

10. A cytoprotective spray dried solid formed from an exogenously acidified liquid aluminum hydroxide containing composition acidified to a pH at which the aluminum hydroxide content is solubilized and obtained by exogenous acidification of a precursor aluminum base containing antacid composition followed by spray drying.

11. The cytoprotective spray dried solid of claim 10 wherein the aluminum base containing antacid composition also contains magnesium hydroxide.

12. The cytoprotective spray dried solid of claim 10 wherein the aluminum base containing antacid composition is magaldrate gel.

13. The cytoprotective spray dried solid of claim 10 wherein the aluminum base containing antacid composition is aluminum hydroxide gel.

14. The method of inducing cytoprotection in humans by increasing the natural defences of the gastrointestinal mucosa which comprises administering to a human in need of such therapy a cytoprotective-effective amount of an exogenously acidified aluminum hydroxide containing composition acidified to a pH at which the aluminum hydroxide content is solubilized.

15. The cytoprotective spray dried solid formed by spray drying a composition of claim 7.

16. The cytoprotective spray dried solid formed by spray drying a composition of claim 8.

* * * * *